United States Patent
Breynaert et al.

(10) Patent No.: US 11,500,044 B2
(45) Date of Patent: Nov. 15, 2022

(54) NUCLEAR SPIN HYPERPOLARIZATION IN A POROUS MATRIX

(71) Applicant: Bruker France SAS, Wissembourg (FR)

(72) Inventors: Eric Breynaert, Bever (BE); Johan Martens, Huldenberg (BE); Francis Taulelle, Leuven (BE); Pieter Leo Hendrik Verlooy, Grimbergen (BE); Jean-Max Tyburn, Wissembourg (FR); James Kempf, Arlington, MA (US)

(*) Notice: Subject to any disclaimer, the term of this patent is extended or adjusted under 35 U.S.C. 154(b) by 239 days.

(21) Appl. No.: 16/970,906

(22) PCT Filed: Feb. 19, 2019

(86) PCT No.: PCT/IB2019/051342
§ 371 (c)(1),
(2) Date: Aug. 18, 2020

(87) PCT Pub. No.: WO2019/159154
PCT Pub. Date: Aug. 22, 2019

(65) Prior Publication Data
US 2020/0386833 A1    Dec. 10, 2020

Related U.S. Application Data

(60) Provisional application No. 62/633,260, filed on Feb. 19, 2018.

(51) Int. Cl.
| | | |
|---|---|---|
| *G01R 33/00* | (2006.01) | |
| *G01R 33/28* | (2006.01) | |
| *A61K 49/18* | (2006.01) | |
| *G01R 33/30* | (2006.01) | |
| *G01R 33/56* | (2006.01) | |

(52) U.S. Cl.
CPC ........ *G01R 33/282* (2013.01); *A61K 49/1833* (2013.01); *G01R 33/302* (2013.01); *G01R 33/305* (2013.01); *G01R 33/5605* (2013.01)

(58) Field of Classification Search
CPC .............. G01R 33/543; G01R 33/5608; G01R 33/4828; G01R 33/3415; G01R 33/283;
(Continued)

(56) References Cited

U.S. PATENT DOCUMENTS

| 8,766,633 B2* | 7/2014 | Bhattacharya | ......... G01R 33/30 324/309 |
|---|---|---|---|
| 2010/0219826 A1* | 9/2010 | Duckett | ................. A61K 49/06 324/307 |
| 2014/0125334 A1* | 5/2014 | Owers-Bradley | .... G01R 33/282 324/309 |

FOREIGN PATENT DOCUMENTS

WO    2017085220 A1    5/2017

OTHER PUBLICATIONS

Rouquerol, J et al., "Recommendations for the Characterization of Porous Solids", Pure and Applied Chemistry, vol. 66, No. 8, pp. 1739-1758 (1994).
(Continued)

*Primary Examiner* — Jermele M Hollington
*Assistant Examiner* — Taqi R Nasir
(74) *Attorney, Agent, or Firm* — Benoit & Côté Inc.

(57) ABSTRACT

A method of enhancing the nuclear spin polarization of target molecules (10) uses a hyperpolarized source material (12) that is co-confined with the target molecules (10) in a porous molecular matrix (20). The matrix (20) may be a D4R-polysiloxane copolymer such as polyoligosiloxysilicone number two (PSS-2) that has recesses of an appropriate diameter. A source material (12), such as parahydrogen, is transferred to the matrix (20) together with the target molecules (10), and an external pressure is applied to force them into the recesses of the matrix (20). The nano-confinement of the source material (12) and target molecules (10) together enables or enhances a transfer of spin polarization from the source material (12) to the target molecules (10).
(Continued)

When the target molecules (10) are removed from the matrix (20), the enhanced spin polarization greatly enhances the signal strength of the target molecules (10) in any subsequent magnetic resonance measurement.

14 Claims, 9 Drawing Sheets

(58) Field of Classification Search
CPC .... G01R 33/307; G01R 33/60; G01R 33/282; G01R 33/302; G01R 33/305; G01R 33/5605; G01V 3/32; E21B 49/08; E21B 2049/085; G01N 24/10; A61K 49/1833
See application file for complete search history.

(56) References Cited

OTHER PUBLICATIONS

Obenaus, Utz, et al., "Parahydrogen-Induced Hyperpolarization inside Meso- and Micropores of Pt-, Rh-, Ir-, and Pd-Containing Solid Catalysts", Journal of Physical Chemistry C, vol. 121, No. 18, Apr. 18, 2017.
Bouchard L-S et al., "Para-Hydrogen-Enhanced Hyperpolarized Gas-Phase Magnetic Resonance Imaging", Angewandte Chemie, International Edition, Wiley-VCH, DE, vol. 46, No. 22, Apr. 23, 2007.
Roth, Meike, et al. "Continuous 14H and 13C Signal Enhancement in NMR Spectroscopy and MRI Using Parahydrogen and Hollow-Fiber Membranes", Angewandte Chemie, International Edition, Wiley-VCH, DE, vol. 49, 10.45, Oct. 29, 2010.
Lehmkuhl, Sören, et al., "Continuous hyperpolarization with parahyrogen in a membrane reactor", Journal of Magnetic Resonance, Academic Press, Orlando, FL, US, vol. 291, Mar. 31, 2018.
Rouquerol, J et al., "Liquid intrusion and alternative methods for the characterization of macroporous materials (IUPAC Technical Report)", Pure Appl. Chem., vol. 84, No. 1, pp. 107-136, 2012.
Nikolaou, Panayiotis, "NMR Hyperpolarization Techniques for Biomedicine", Chemistry, 2015.
Galarneau, Anne, et al., "Validity of the t-plot Method to Assess Microporosity in Hierarchical Micro/Mesoporous Materials", Langmuir, Sep. 18, 2014.
Bals, Sara, "Quantitative Three-Dimensional Modeling of Zeotile Through Discrete Electron Tomography", J. Am. Chem. Soc., 2009, 131 (13), pp. 4769-4773.

* cited by examiner

NUCLEAR SPIN HYPERPOLARIZATION IN A POROUS MATRIX

BACKGROUND OF THE INVENTION

Field of the Invention

This invention relates generally to the field of magnetic resonance analysis of sample materials and, more specifically, to the nuclear spin polarization of samples for analysis using magnetic resonance measurement techniques.

Description of the Related Art

Nuclear magnetic resonance (NMR) is a phenomenon in which certain atomic nuclei become magnetically polarized in proportion to an applied magnetic field and, as a result, will absorb and re-emit electromagnetic radiation. It serves as the basis for certain measurement techniques, including magnetic resonance imaging (MRI) and NMR spectroscopy. One difficulty with measuring NMR signals is their relatively low signal strength, which requires powerful magnets, typically using superconducting magnetic coils that need extreme cooling in a cryogenic environment.

Nuclei susceptible to NMR have an inherent nuclear "spin" associated with their magnetic moment, with a spin polarization that is aligned by the external magnetic field. The degree of these polarizations tends to be relatively low, for example, a parts-per-million scale preference for parallel vs. anti-parallel alignment even at the highest currently achievable values of the applied magnetic field. That contributes to the relatively low signal strength of NMR signals. However, methods of increasing the magnitude of polarization of such nuclei have been used in the past, a process referred to as "hyperpolarization." Typically, nuclei can only be hyperpolarized in special circumstances, and the process is often limited to application with specific nuclei in specific chemical compounds or materials. A common example is the nuclei of molecular hydrogen $H_2$. However, certain methods of transferring hyperpolarization to nuclei of interest have been demonstrated. Of these, the most well-known is dynamic nuclear polarization (DNP), in which the spin polarization of electrons is transferred to the target nuclei, but this process requires extremely low temperatures (as low as 1 Kelvin), microwave irradiation and doping of the sample with a compound containing one or more unpaired electrons. A distinct hyperpolarization method called para-hydrogen induced polarization (PHIP) has also been demonstrated in which parahydrogen (p-$H_2$), the singlet form of the hydrogen molecule, which normally constitutes only about 25% of hydrogen molecules at room temperature, is enriched to a higher percentage and used to transfer spin polarization to other molecules. However, the enrichment of this p-$H_2$ also requires cryogenic conditions and catalytic conversion of the non-para fraction of hydrogen molecules (orthohydrogen, o-$H_2$) into p-$H_2$. Furthermore, the transfer of hyperpolarization from the hydrogen nuclei of p-$H_2$ into a molecule of interest for study by NMR or MRI is a challenging process that can suffer from low concentration of p-$H_2$, poor mixing with target molecules and chemical specificity of their interaction.

SUMMARY OF THE INVENTION

In accordance with the present invention, a method of enhancing the nuclear spin polarization of target molecules is provided that uses a hyperpolarized source material and a nanoporous matrix, such as a matrix in which nanopore sizes are below about 1 micrometer in any given direction. The source material and the target molecules are transferred to the porous molecular matrix, in certain situations along with a fluid solvent, and confined together in nanoscale recesses of the matrix under external pressure for a predetermined period of time, after which the target molecules are removed from the nanoporous matrix. During this period of nano-confinement, hyperpolarization is transferred from the source material to the target molecules, providing them with an enhanced spin polarization that greatly increases the magnitude of the magnetic resonance signal of the target molecules during a subsequent magnetic resonance measurement.

In an exemplary embodiment of the invention, the source material includes parahydrogen, although other source materials may likewise be used. The porous molecular matrix has recesses that are sized to best accommodate the selected source material and target molecules and, in a particular embodiment, may have recesses with an average diameter in any direction of confinement of 1-20 nm. The size of the recesses may be approximately the same throughout the material, or may be varied. In one version of the invention, the porous molecular matrix has recesses of distinctly different sizes, with a first group of recesses being relatively small, while a second group of recesses is relatively large, even including features with one or more dimensions larger than 1 micrometer. In one such embodiment, the smaller recesses may function as storage for the hyperpolarization source material, whose relatively small size, in the example of $H_2$ (or p-$H_2$), may allow it to be loaded to the small recesses at relatively modest pressures (<100 bar, or even <10 bar), while the larger recesses may function as nanoscale chambers accommodating source material and target molecules together while hyperpolarization is transferred from the source material to the target molecules. In another such embodiment, larger recesses and/or channels or irregular pathways in the porous material may serve to transmit both hyperpolarization source material and target molecules, possibly with solvent or carrier fluid, throughout the porous material, while continued application of pressure, possibly to an increased level, serves to load material and target molecules together into smaller, nanoscale recesses for hyperpolarization transfer from the source material to the target molecules.

In yet another such embodiment, the porous material contains recesses and/or channels that are both smaller and larger than the nanoscale recesses for hyperpolarization transfer from the source material to the target molecules. In this case, the features with larger dimensions may serve to transmit source material, target molecules and possibly solvent or carrier fluid to smaller features, including nanoscale recesses for hyperpolarization transfer and still-smaller recesses for storage of source materials. In all embodiments, the delivery of source material and target molecules to the nanoscale recesses for hyperpolarization transfer may be achieved in concert or in sequential steps.

An external pressure may be applied to facilitate co-loading of source and target materials, possibly with a solvent or carrier fluid, into nanoporous regions of the material. The external pressure that is provided during the transfer of hyperpolarization may be substantially constant for the predetermined period during which the source material and target molecules are co-confined in the recesses of the porous molecular matrix. Alternatively, the external pressure may vary significantly during this period, and may vary in a cyclic manner. The amount of external pressure used depends on the matrix material, the source material and the target molecules, and may, for example, be in the range of 0 to 10 bar.

In an exemplary embodiment, the porous matrix material comprises a D4R-polysiloxane copolymer and, in one particular embodiment, the matrix material comprises polyoligosiloxysilicone number two (PSS-2). The matrix material includes recess sizes in the desired range, and is capable of withstanding the external pressure without breaking down.

DETAILED DESCRIPTION

In the present disclosure, the terms 'nanopores' and 'nanoporous' are used to describe walled, caged or windowed enclosures, recesses or channels within a material, in which one or more bounded dimension is in the range of 1 to 1000 nanometers (nm). This range itself encompasses a variety of pore sizes by classical definition [see, e.g., *Pure and Applied Chemistry*, Vol. 66, No. 8, pp. 1739-58 (1994)], including those termed macropores (diameter, D>50 nm), mesopores (D=2-50 nm) and micropores (D<2 nm), and also including confinement in one-dimension, for example between boundaries such as curved or flat material surfaces approaching each other to within <1 micrometer, or confinement in two-dimensions such as within a straight, curved or flexible tube with circular, elliptical, square or irregular cross section that presents one or more directions in which free travel is limited by boundaries at no more than 1 micrometer separation from each other.

Figure 1A:
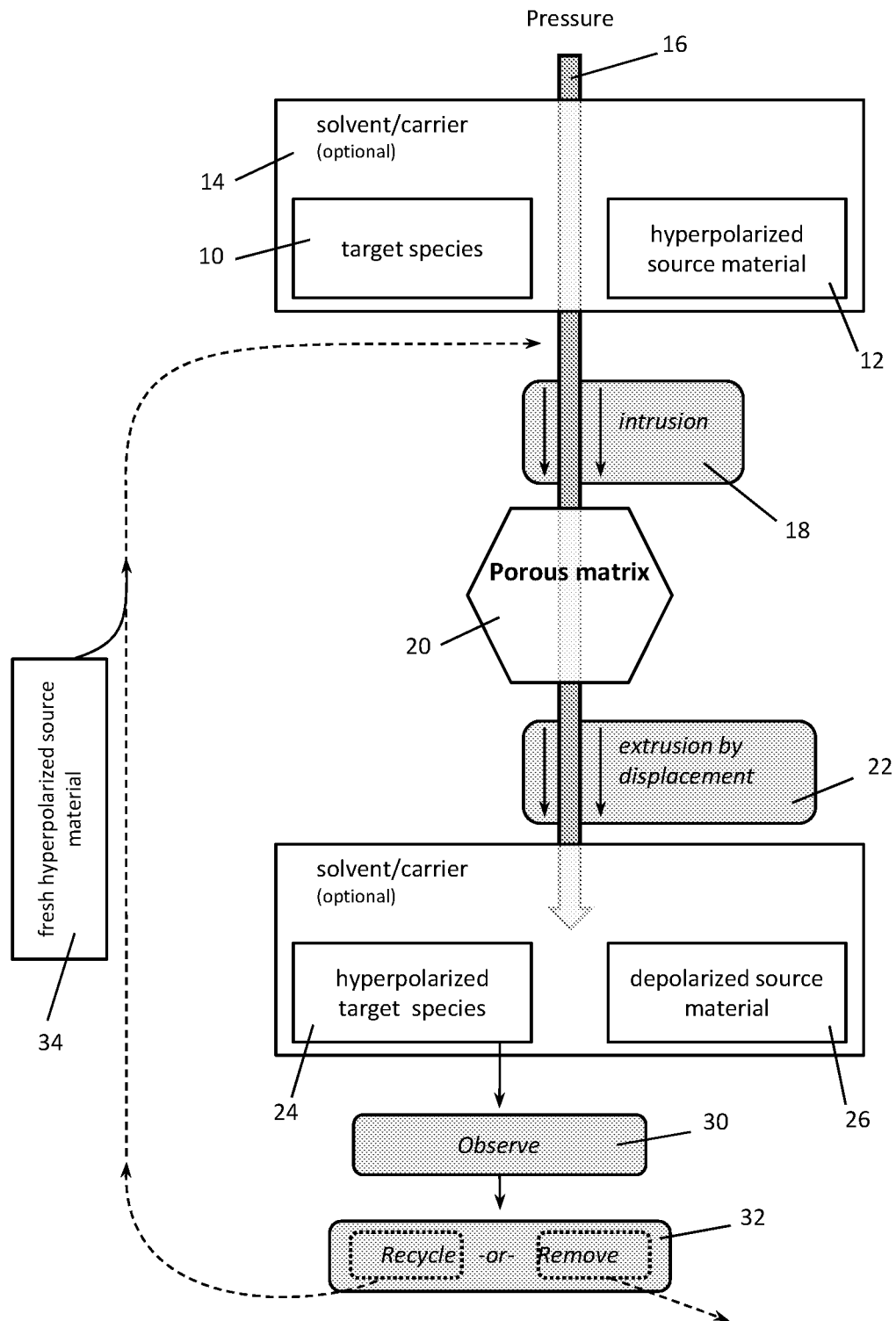
FIG. 1A is a schematic representation of a method of sensitivity enhancement in magnetic resonance according to the present invention, providing an example where substantially constant pressure is applied to implement the invention in a flow-through mode, with hyperpolarization source and target species passing through a nanoporous material.

Shown schematically in FIG. 1A is an overview of one embodiment of the method of hyperpolarizing target molecules according to the present invention. Target molecules of interest 10 are introduced together with a hyperpolarized source material 12, such as parahydrogen or otherwise-hyperpolarized hydrogen, and possibly a solvent or carrier fluid 14, to a porous matrix 20. Solvent or carrier fluid may be useful to facilitate admission and removal of target molecules and/or the hyperpolarization source from the porous matrix. In some cases, the target molecules themselves may constitute a solvent or carrier, and thus an explicit additional fluid may be considered optional. Using a source of pressure 16, the source material, target molecules and optional solvent or carrier are forced into intimate contact with each other upon intrusion 18 into the nanoporous recesses of the matrix 20. Within the confines of the porous material, a transfer of spin polarization from the source material 12 to the target molecules 10 is effected, after which the hyperpolarized target molecules 24 are removed from the matrix (extrusion 22). In the embodiment represented in FIG. 1A, extrusion occurs in a flow-through manner, in which components in the porous matrix are displaced, and extruded therefrom, by an incoming stream of newly intruding components. This removal of hyperpolarized target species may coincide with removal of partially or fully depolarized source material 26, or removal of hyperpolarized target and depolarized source materials may occur successively according to each component's relative rate of passage through a given matrix and for particular conditions of pressure and temperature.

Figure 1B:
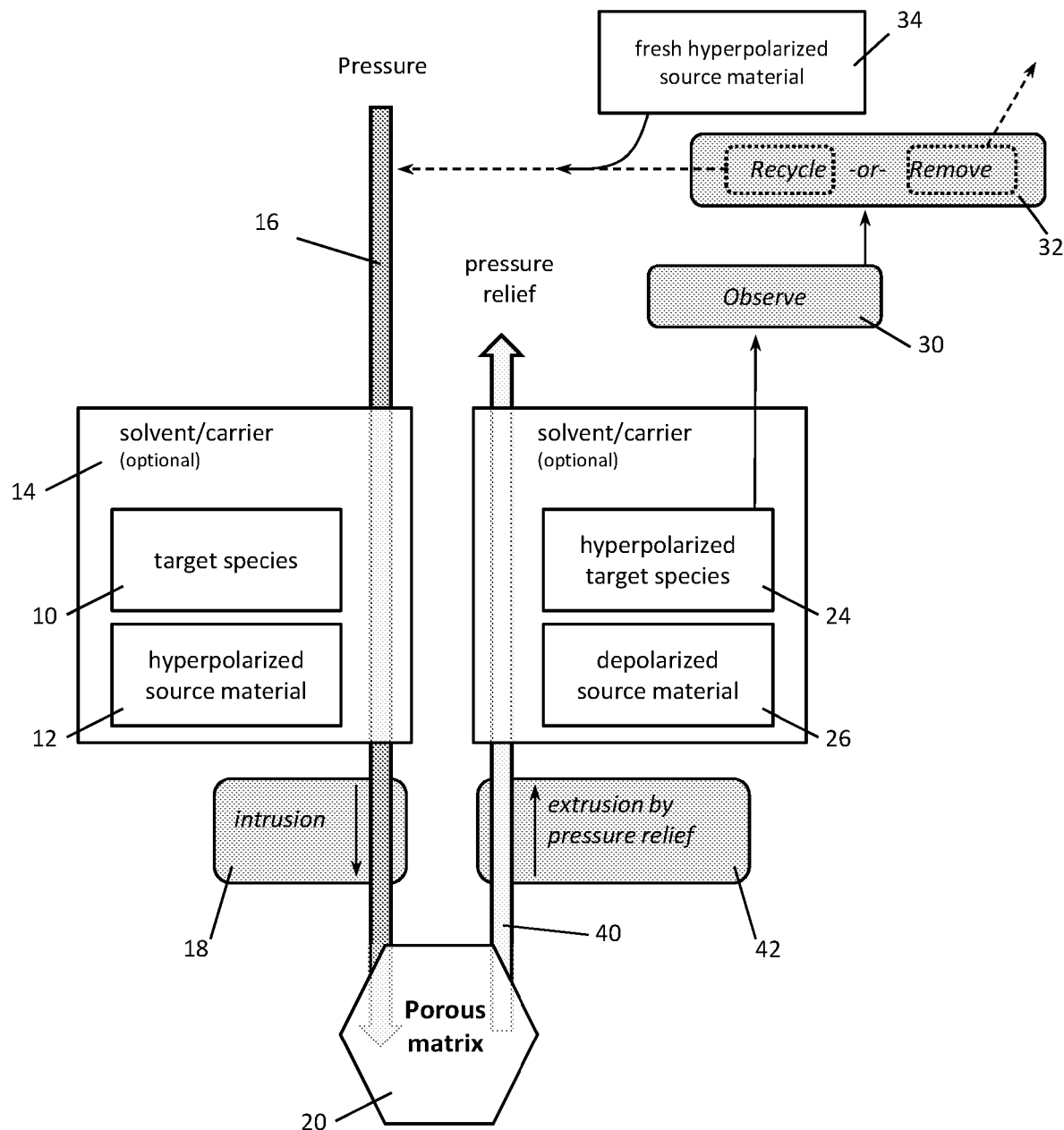
FIG. 1B is a schematic representation similar to FIG. 1A, but for an embodiment of the invention that utilizes a cycle between a high and low-or-zero applied pressure.

FIG. 1B provides overview of another embodiment in which intrusion and extrusion are instead achieved by modulating the pressure between high and low values. Here, as in FIG. 1A, target molecules 10 are introduced with hyperpolarized source material 12, and possibly a solvent or carrier fluid 14, to a porous matrix 20, where pressure 16 applied to a maximum value effects intrusion 18 of target and source species (and optional solvent or carrier fluid) and establishes their intimate contact with each other within the nanoporous recesses of the matrix 20. This again provides for the transfer of spin polarization from the source material 12 to the target molecules 10, allowing for extrusion 42 of hyperpolarized target molecules 24 from the matrix. However, in the embodiment represented in FIG. 1B, extrusion occurs upon setting the pressure to a minimum value, which causes hyperpolarized target species 24 to leave the nanoporous recesses of the matrix, together or in sequence with the departure of depolarized source material 26 and optional solvent or carrier fluid. The distinction between FIGS. 1B and 1A is primarily in the protocol for applied pressure and corresponding modes of intrusion/extrusion. The scheme of FIG. 1B utilizes a pressure cycle between maximum (intruding) and minimum (extruding) values, whereas FIG. 1A depicts relatively constant application of high pressure for purposes of both intruding and extruding.

The key value of both embodiments is their provision of hyperpolarized target materials for observation 30 of hyperpolarized NMR or MRI signals. Typically, and as depicted in both FIGS. 1A and 1B, observation follows extrusion, although it may instead precede that step according to needs of the user. Additionally, in either embodiment, post-observation handling 32 may be employed to either recycle components for combination with fresh hyperpolarized source material 34 and a new round through the process, starting with intrusion, or those components may be removed for disposal or later use.

The transfer of hyperpolarization within the porous matrix may occur by one or more mechanisms, which are enhanced or enabled by the intimate co-confinement of the source material and the target molecules, as provided by the nanoporous matrix. This may include modified spatial ordering of one or both components (source and/or target) due to their concurrent interaction with the matrix and/or its division of components into high surface-to-volume ratio bubbles or droplets within the nanoporous regions. The noted transfer of hyperpolarization may proceed in the presence of a coordinated metal catalyst like those required by prior art parahydrogen-based methods. However, transfer of hyperpolarization in the porous matrix may also be achieved in the absence of such a catalytic metal center. Furthermore, the specific conditions typical of DNP, such as microwave radiation and cryogenic temperatures, are not required and are generally omitted, except perhaps in cases where much more modest cryogenic temperatures, for example >100 K, may be utilized to alter the kinetics of molecular interaction. As such, the present invention provides a simple, low-cost method of hyperpolarizing target molecules of interest.

To discuss hyperpolarization in the case where it is derived from p-$H_2$, it is helpful to first define the molecule, which is a particular spin-isomer of the hydrogen molecule, $H_2$. All $H_2$ molecules can be considered as two protons chemically bound by two electrons. When two spin-½ nuclei, such as the pair of proton nuclei in hydrogen atoms, are combined, they may exist in either a singlet state (referred to as parahydrogen or p-$H_2$) or in one of three triplet states (collectively referred to as orthohydrogen, or o-$H_2$. These forms reflect the manner in which the two spins-½ are paired. For a triplet, two of the possible pairings correspond to parallel co-alignment of the two spins, that is, either both spins up ($\uparrow\uparrow$) or both down ($\downarrow\downarrow$) with respect to the direction of an externally applied magnetic field. The third state in the ortho set is a symmetric superposition of two antiparallel spin pairs ($\uparrow\downarrow+\uparrow\downarrow$)/$2^{1/2}$, where the factor of $½^{1/2}$ is for mathematical normalization such that this pair of pairs may be properly used to represent a single pair of spins. The existence and physical meaning of such a superposition is somewhat counterintuitive, but nonetheless, a widely known, accepted and understood phenomenon of quantum physics.

Finally, the parahydrogen spin state is the anti-symmetric variation of the above superposition, namely ($\uparrow\downarrow-\uparrow\downarrow$)/$2^{1/2}$, with the minus sign replacing the plus sign in ($\uparrow\downarrow+\uparrow\downarrow$)/$2^{1/2}$. Although the singlet state (p-$H_2$) is the energetic ground state, the very small energy difference between the singlet state and the three triplet states results in an almost exact 75/25 ratio of o-$H_2$ to p-$H_2$ at room temperature, that is, an essentially equal population of all four spin states. However, in cryogenic conditions, cold enough that the available thermal energy drops near or below the energy difference between singlet and triplet states, it becomes possible to capture >25% of the hydrogen molecules in the para form, including >90% p-$H_2$ at temperatures near 30 K.

To achieve such enrichment in a reasonable amount of time, the conversion is typically performed in the presence of a paramagnetic catalyst or charcoal. When $H_2$ interacts with such a catalyst or surface, the symmetry of the molecule is transiently broken such that quantum-mechanical rules against interconversions between o-$H_2$ and p-$H_2$ are relaxed. This allows relatively rapid equilibration of the 75% o-$H_2$ derived from room-temperature $H_2$ to a much lower fraction dictated by the lower thermal energy available at cryogenic temperatures. This enrichment of the p-$H_2$ fraction persists when removing or displacing the cryogenically and catalytically equilibrated hydrogen molecules from the catalyst. When subsequently kept in a suitably inert, non-catalytic environment, parahydrogen enrichment levels as high as 50, 90 or even 99% can persist for weeks to months at room temperature. Thus, it becomes a long-lived reservoir of non-Boltzmann (non-thermal-equilibrium) spin order that has been utilized to transfer hyperpolarization into nuclear spins of other molecules via chemical reactions that again break the symmetry of the $H_2$ molecule.

Applications of p-$H_2$ are found in the field of NMR or MRI to enhance sensitivity by transfer of the hyperpolarization to a molecule of interest. In NMR or MRI experiments, the measured signal is directly proportional to the difference in population among various energy states. The states and their energies mainly differ according to orientations of nuclear spin magnetization with respect to an externally applied magnetic field. In normal circumstances, the population differences are rather small, typically on the scale of tens of parts-per-million (ppm), or near 0.001% preference for one spin orientation over another. However, in the extreme of nearly pure p-$H_2$, essentially all available hydrogen molecules share the same energy state and a vanishing fraction populate the ortho states. Such a huge difference in spin populations is the very essence of hyperpolarization, and can result in a massive increase in signal intensities for NMR or MRI (up to a factor of $10^5$).

Using this feature of p-$H_2$ in practice, however, requires transfer and conversion of the spin order provided by p-$H_2$ into other target molecules. This demands the use of non-interacting materials to prevent relaxation of the hyperpolarization until it is ready for transfer, as well as expert execution of subsequent physical and chemical steps to effect the noted transfer and conversion, and, in some cases, additional efficient delivery of the products to NMR or MRI equipment for observation. This is essential for the design of equipment for generating and reacting p-$H_2$, and observing consequent signal enhancements by NMR or MRI.

There are various known chemical means to transfer hyperpolarization from p-$H_2$ to a target species. The earliest approach involves a hydrogenation reaction between p-$H_2$ and an unsaturated organic compound. Later, a non-hydrogenative method was discovered, involving transient interaction among a catalyst and various substrates, including p-$H_2$ and target molecule(s). The hydrogenative methods are often generally referred to as PHIP (parahydrogen induced polarization), or somewhat more specifically as PASADENA (parahydrogen allows dramatically enhanced nuclear alignment), or ALTADENA (adiabatic longitudinal transport and dissociation engenders nuclear alignment) experiments. The non-hydrogenative case with transient catalytic interaction is often referred to as NH-PHIP or somewhat more specifically as the SABRE (Signal Amplification by Reversible Exchange) experiment.

By the methods of the present invention, hydrogenative PHIP and NH-PHIP may be carried out within nanoporous materials, enabling adjustment of the physicochemical conditions of the underlying chemical interactions, and corresponding improved hyperpolarization transfer from p-$H_2$ to target species. Conditions modulated and improved by nano-confinement include, for example, increased solubility of p-$H_2$, altered kinetics and equilibrium populations in the underlying chemical interactions and even altered structure of compounds involved, an effect that can modulate spin-spin couplings required for hyperpolarization transfer.

Beyond PHIP and NH-PHIP, there are other means of hyperpolarization transfer without complete or reversible (catalytic) chemical reaction, which rely instead on the mere vicinal approach of the source and target species. This may include the introduction of spin-spin couplings known as residual dipolar couplings (RDCs), which occur on spatial confinement and/or partial alignment of molecules. For example, RDCs useful for hyperpolarization transfer may be introduced for nuclear spins within p-$H_2$ and/or target molecules when they are confined to chambers or recesses of a porous material.

In the present invention, the specific material used for the porous matrix is important to ensure that the co-confining of the source and target effectively and efficiently enables a desired transfer of polarization. The porosity of the material is on a scale that is often referred to as "nanoporous" and, for best performance in the context of the present disclosure, should be a material with pores having an average diameter in the range of 1-20 nm. In particular, the pores should be small enough to exhibit the characteristic effects of nano-confinement, enhancing or enabling the transfer of hyperpolarization through intimate co-confinement of the source material and the target molecules within the porous matrix. As a characteristic dimension of small molecules, such as water, is below about 0.5 nm, a pore size of 20 nm or more would result in an average diameter measuring about forty molecules across, at which point the effects of nano-confinement would diminish. It is likewise important that the pores are not too small, as this would require a very high amount of pressure (e.g., over 100 bar) to force the liquid into the recesses of the material, and could exclude larger target molecules of interest from the recesses.

Figure 2C:
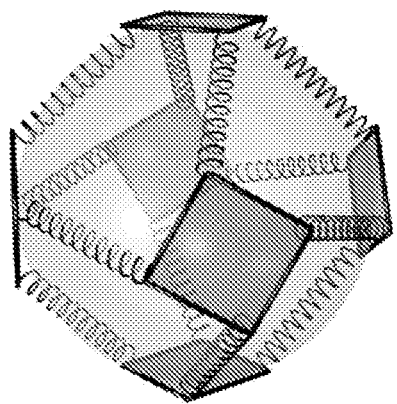
FIG. 2C is a schematic depiction of one of the single small cavities designated "a" in FIG. 2A. Faces of the D4R units, represented by shaded squares and springs representing linkers between D4R units form the windowed boundaries of the cavity.
Figure 2D:
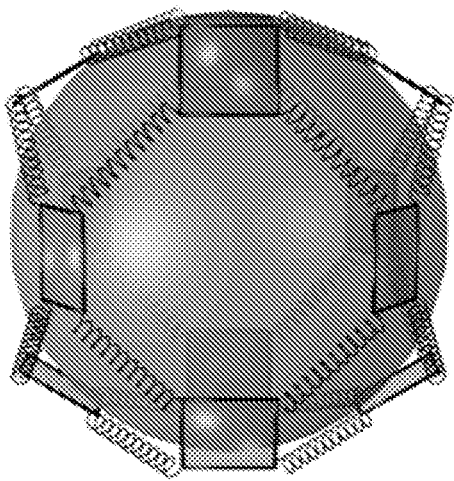
FIG. 2D is a schematic depiction of one of the large cavities, designated "b" in FIG. 2A. As in FIG. 2C, springs and shaded squares represent, respectively, linkers between, and faces of, D4R units, whereas the sphere represents the cavity within the windowed boundaries.

In one embodiment of the invention, the porous material has a heterogeneous or hierarchical arrangement of pore sizes. For example, FIG. 3A shows an SEM picture of a region within a PSS-2 sample that exhibits heterogeneous porosity. Pores having a diameter of <5 nm, like those described in conjunction with FIGS. 2A-2D, are present in the material, but not visible in FIG. 3A due to an SEM resolution near 3-4 nm. However, a variety of larger pores sizes are clearly displayed in boxed regions labeled 'a', 'b' and 'c'. Region 'a' alone contains a random heterogeneous distribution of pores being about (17±3) nm in diameter. These pockets are formed during the linkage step of synthesis when HCl gas bubbles are generated within the developing material. A larger pore scale (openings of about 50-100 nm in diameter) is apparent in region 'b' and, finally, region 'c' is a much larger cavity with >500 nm characteristic scale. A separate example, in this case of a hierarchical material (Zeotile-4) with nanopores at various characteristic dimensions, is depicted in the SEM image of FIG. 3B. The inset 'a' zooms to a hexagonal pillar containing many cylindrical channels, each with free internal diameter of about 7.5 nm and lengths up to several microns. These are generated by cylindrical template micelles that are present during the synthesis of Zeotile-4 and which are removed post-synthetically by calcination. (See, e.g., Sara Bals, et al., Quantitative Three-Dimensional Modeling of Zeotile Through Discrete Electron Tomography, *Journal of the American Chemical Society*, 2009 131 (13), 4769-4773). The inset 'b' provides an alternative side-on view of a similar structure, although one where the hexagonal pillar curves slightly. This alternative view highlights distinct pores, referred to as side pockets whose access windows range from 2 to 3 nm. These pores occur with a specific structural relation to those highlighted in inset 'a', and are thus referred to as hierarchical.

In the cases of heterogeneous or hierarchical porosity, as long as some fraction of the pores falls within the desired range for nanoconfinement, then the desired effect could still be realized. Moreover, if smaller pores were interspersed with those in the range of 1-20 nm, the smaller pores could function as a storage location for a source material, such as parahydrogen, having a smaller molecular size than target and/or solvent molecules. The large pores could then function as chambers for accommodating the interaction between the source material and the target molecules. At the same time, still larger features, such as pores, channels or interstitial spaces between regions including the smaller features, may provide efficient pathways for broad and nearly uniform distribution of source and target species to nanoscale and smaller recesses of the porous material, as well as efficient removal following hyperpolarization transfer from source to target.

The application of pressure is important to the process, but the pressure may be applied in different ways. In one embodiment, the pressure is elevated for both intrusion and extrusion steps. This would be particularly useful, for example, if the system was operating in a "flow-through" arrangement, as depicted in FIG. 1A. For example, a given constant pressure could be used to drive a continuous supply of target and hyperpolarized source species into the nanoporous regions. Those species would experience an average time of co-residence within nanopores that allows transfer of hyperpolarization from source to target, while the continuous stream of fresh input would eventually displace the hyperpolarized targets and depolarized source molecules.

In another embodiment, the pressure is varied during the process and, in particular, may be cyclic. That is, the pressure level may be varied repeatedly between a minimum pressure level and a maximum pressure level during the course of the process, as depicted in FIG. 1B. In this way, the maximum pressure condition would serve to load fresh target and hyperpolarized source species to the nanoporous regions, and some intermediate-to-maximum pressure level would be maintained for a time during which co-residence within nanopores allows sufficient transfer of hyperpolarization from source to target. Following this, reduction to a minimum pressure would allow release of hyperpolarized targets and depolarized source molecules. The cycle could then be repeated for subsequent rounds of hyperpolarization transfer.

In either embodiment, extrusion or release of hyperpolarized target molecules from the nanopores, possibly including their complete removal and separation from the material, may then be followed by additional transfer or transfers of hyperpolarization between nuclei in the extruded sample. Such additional transfers may be either intramolecular, for example, using INEPT (insensitive nuclei enhanced polarization transfer) pulse sequences, or cross polarization (CP) methods, or intermolecular, for example, using NOEs (Nuclear Overhauser Effects), other dipole-dipole interactions or chemical exchange. Also following extrusion, and either with or without such additional transfers, observation of NMR or MRI signals from the target species and/or subsequent targets of additional steps to transfer hyperpolarization, may also be performed, with corresponding gains in sensitivity due to the hyperpolarization. As another option, NMR or MRI observation may be applied to hyperpolarized species within the porous matrix, before extrusion. Regardless of the timing of observation, after extrusion one may choose to remove the observed components for disposal or later use, or to recycle them for reinsertion to the process with fresh hyperpolarized source material.

Porous Matrix

In an exemplary embodiment of the invention, a polyoligosiloxysilicone, designated "PSS-2," is used as the porous matrix. Silicones are polysiloxanes with formula [—SiRR'—O]n, and have excellent heat and radiation resistance, as well as good mechanical and chemical stability. These polymers contain a linear or branched backbone consisting of alternating silicon and oxygen atoms, decorated with organic groups R and R' attached to Si atoms. The most commonly used linear example is polydimethylsiloxane, with equivalent R and R' species being methyl groups. Branched polysiloxanes have particular application in chromatography, electronics, coatings and medicine. They are typically synthesized by polycondensation of multifunctional silane monomers, or by copolymerization processes involving branch point molecules. With its eightfold functionality (that is, eight chemically reactive corners), the highly symmetrical octameric double four ring cyclosilicate (D4R) constitutes an ideal branch point, useful, for example, in the formation of porous three-dimensional (3D) structures.

The present invention exploits advantageous physicochemical properties of polysiloxanes (flexibility, chemical resistance, heat stability, etc.) in chemical applications, in particular, by utilizing a porous 3D framework of polysiloxanes, preferably arranged in a repetitive fashion, yielding structural order. In some cases, such order may be masked to techniques like X-ray crystallography due to structural flexibility and motion, or to a temporarily collapsed (deflated) state of the structure. However, whether masked or not, such order is of value to the present invention. Hyperpolarized source and target species, and optional solvent or carrier fluid, may be loaded and unloaded to nanoporous recesses within PSS-2 or other polysiloxane material via continuous or variable application of pressure.

Figure 2A:
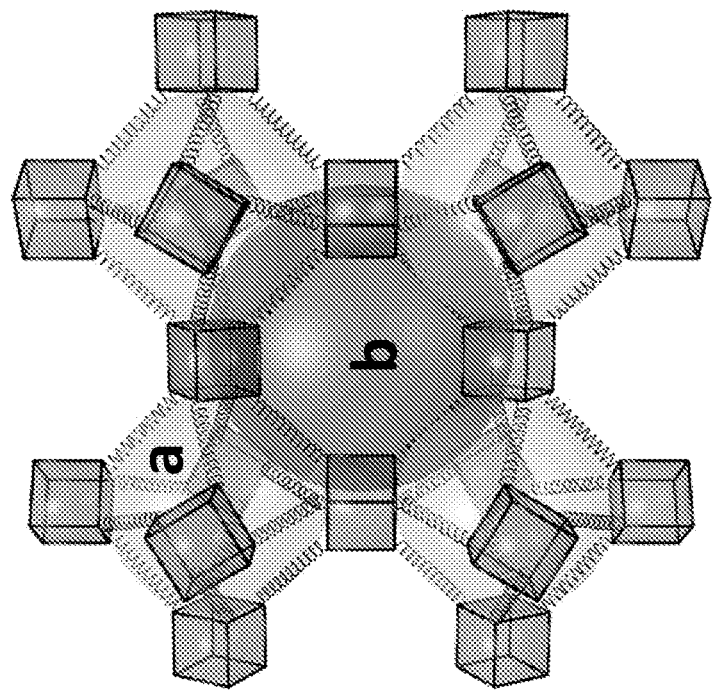
FIG. 2A is a schematic depiction showing a linking pattern with cubic D4R units (darker shaded regions) resulting in small cavities (one of which is labeled "a" with lightly shaded boundary windows) and large cavities (one of which is labeled "b" and here filled with a shaded sphere as a representative highlight). D4R units are joined at the corners by linkers, here shown as springs representing covalent- or hydrogen-bonded chains.
Figure 2B:
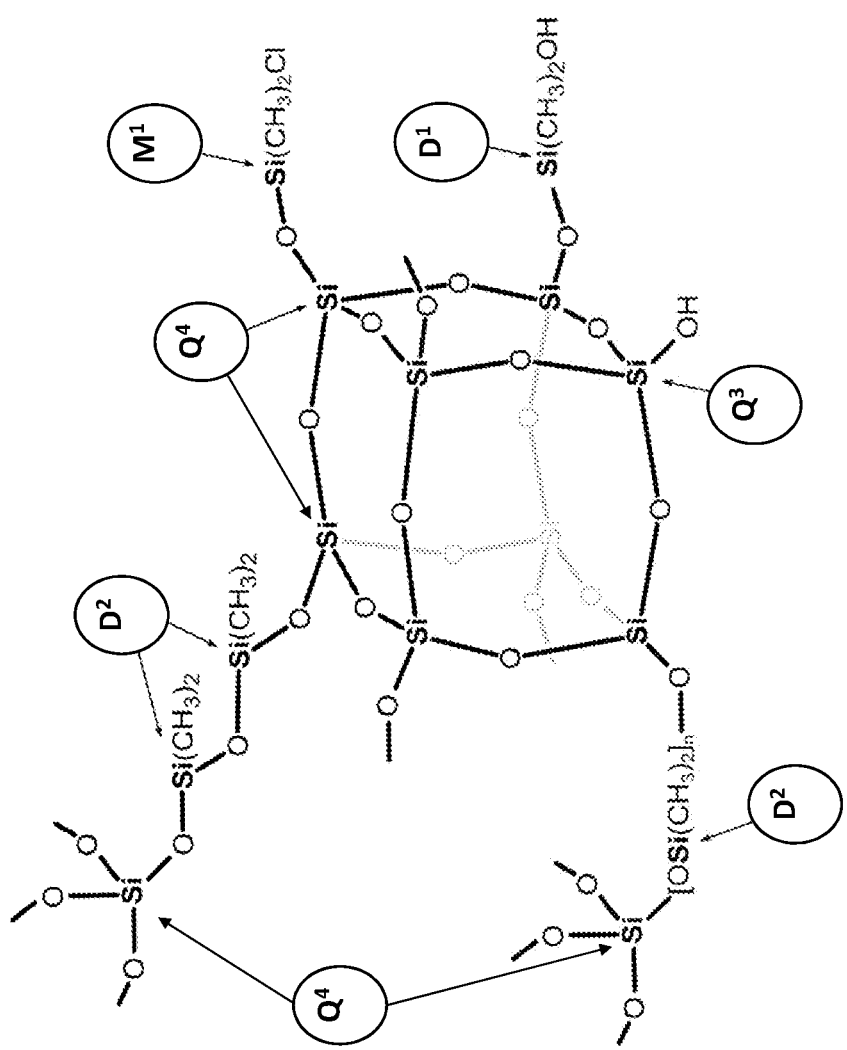
FIG. 2B is a rendering of the chemical structure of the octameric double-four-ring (D4R) silicate unit depicted as shaded cubes in FIG. 2A. The decoration whereby corners of the D4R unit are modified with silicone side chains, exemplifies the chemical branching structure utilized to make a nanoporous material like that shown in FIG. 2A.
Figure 3A:
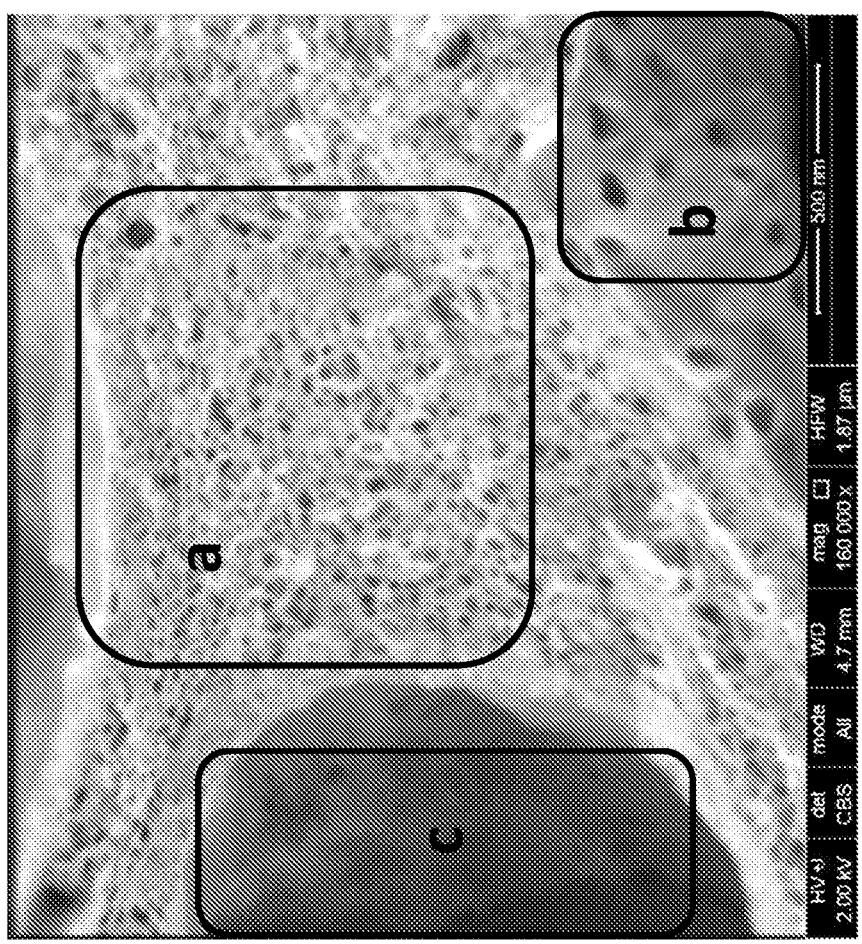
FIG. 3A is a scanning electron micrograph (SEM) picture of an example material, PSS-2, showing heterogeneous porosity, where boxed regions 'a' (17±3 nm), 'b' (50-100 nm) and 'c' (>500 nm) exemplify pores on distinct size scales in a material that also contains nanopore features to <5 nm diameter, which is beyond the resolution of the image.
Figure 3B:
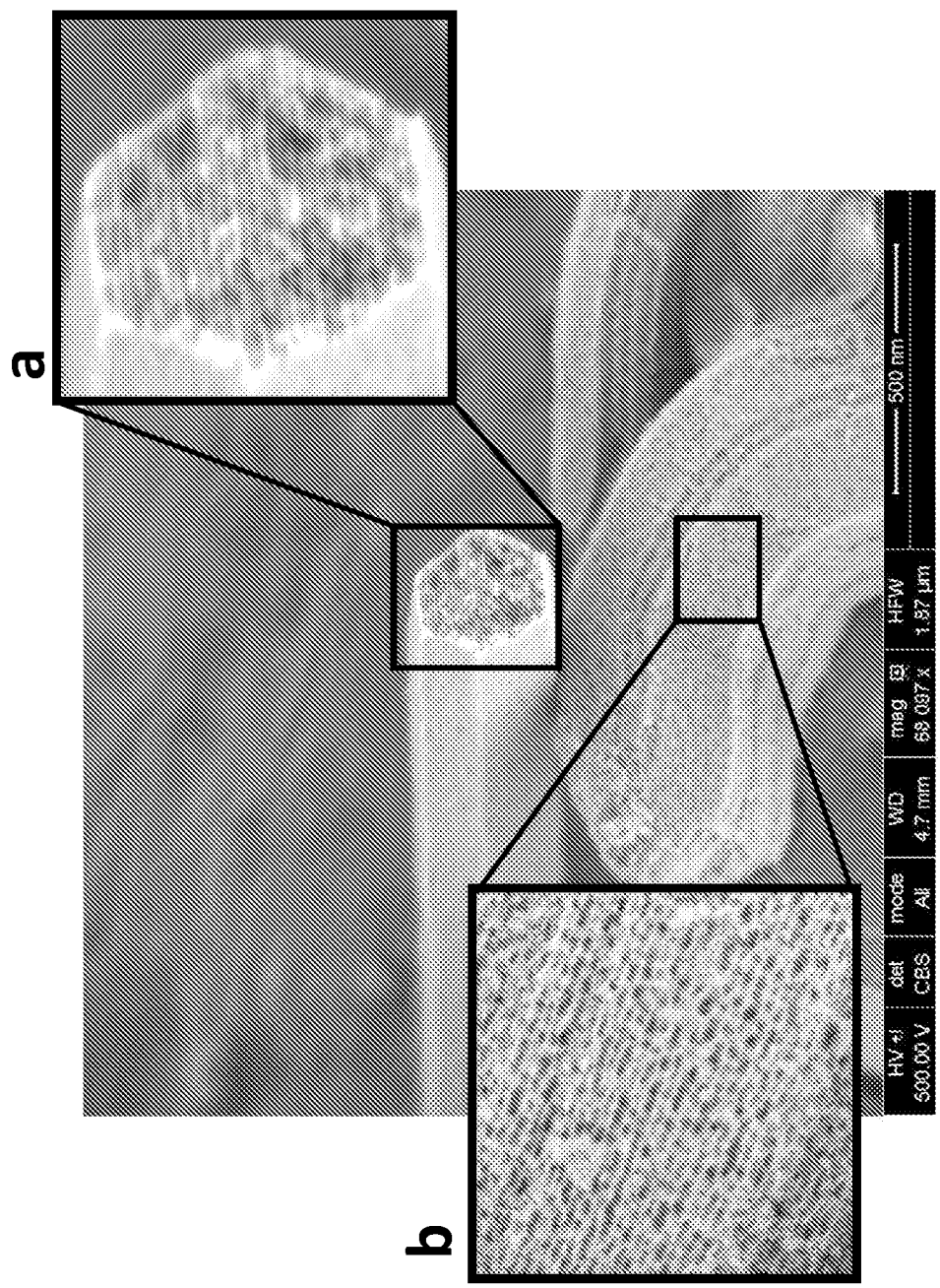
FIG. 3B is an SEM picture of an example material, Zeotile-4, exhibiting hierarchical porosity. The inset 'a' provides a zoomed view of a hexagonal pillar containing many cylindrical mesopore channels, each with free internal diameter of about 7.5 nm. The inset 'b' provides an alternative side-on view of a similar structure, although one where the hexagonal pillar curves slightly. The zoomed region b highlights distinct pore dimensions, referred to as side pockets whose access windows range from 2 to 3 nm.

In PSS-2, the D4R units are arranged in a 3D repetitive structure like that shown schematically in FIG. 2A which, in addition to the D4R interior, provides two cavity types, labeled 'a' (small cavities) and 'b' (large cavities). FIG. 2B shows a D4R unit at atomic detail, including Si atoms present at D4R corners and those in segments attached to the corners. For example, on the right-hand side of this depiction, three of the corners are shown with terminating groups, which lack connection to a further D4R unit. Also, at left in FIG. 2B, examples shown include dimethylsiloxane chains that link corners ($Q^4$ Si atoms) of distinct D4R units in the material. At lower left, a chain of n repeating $D^2$ dimethyl siloxane groups joins to a Si atom at the corner of an adjacent D4R unit. At upper left, a linker is shown for the case n=2. Porous materials may be formed with either mixed-length linkers or relatively uniform linkers. In the example of uniform n=2 linkers, similar-sized pore types a and b result with diameters of about 1-2 nm. Cases with matching linkers at all eight corners for all or nearly all D4R units in the material can result in a more ordered large-scale structure. Nonetheless, even non-uniform linkages can provide nanoporous qualities of use in the present invention. Finally, FIGS. 2C and 2D are zoomed views of isolated small and large cavities from FIG. 2A.

NMR analysis of resolved $^{29}$Si signals from the various Si-atom types offers a means to characterize the degree of cross-linking and chain lengths of the linkers. The variety of Si sites present in this example includes types labeled as $Q^4$ (bonding to 4 oxygen atoms, each providing another Si atom as a next-nearest neighbor to the first), $Q^3$ (similarly, but one of 4 oxygens not bonded to another Si atom), $D^2$ (bonded to two oxygen atoms, each connected to a subsequent Si atom), $D^1$ (bonded to two oxygens, but only one connected to a subsequent Si atom) and $M^1$ (bonded to only one oxygen atom, which itself is bonded to a subsequent Si atom). The degree of connectivity (cross linking of the D4R cubes) is approximately determined from the areas $A_{Q3}$ and $A_{Q4}$ of $^{29}$Si NMR peaks from $Q^3$ (—OH terminated D4R corners) and $Q^4$ (linked D4R corners), such that fractional connectivity of the corners is given by $A_{Q4}/(A_{Q3}+A_{Q4})$. Similarly, peak areas corresponding to other Si-atom types reveals impurity levels and side products. For example, unlinked $D^2$ sites exhibit a narrow $^{29}$Si NMR peak near −21 ppm, whose area can be used to determine the amount of polydimethylsiloxane side product, whereas peaks for $D^2$ sites in the linkers of PSS-2 are much broader and appear near −16 ppm. Similarly, a peak for $D^1$ sites at −9 ppm characterizes the amount of broken linkers, and another type of site, $Q^2$ (not present in FIG. 2B) exhibits a peak at −91 ppm whose area determines the quantity of collapsed cubes, where one or more edges of the D4R unit are broken.

Porous polysiloxanes have been generated in the past by the addition of sacrificial templates or by foaming techniques applied during cross linking. However, the introduction of porosity in branched polysiloxanes built up from cross linked D4R units has rarely been achieved, and has generally not yielded desired regular patterns of structure. For example, D4R-polysiloxane copolymers have been obtained by reaction of dimethyldichlorosilane with D4R cyclosilicate molecules dissolved in water. In that case, the high water concentration prevents controlled polymerization due to the occurrence of unwanted side reactions between Si—Cl sites and water, leading to random D4R-polysiloxane copolymers. In addition, undesirable side reactions can generate freestanding or dangling dimethylsiloxane oligomers.

One recently presented option to reduce the water concentration in the system is to use cyclosilicate hydrate (CySH) crystals as a source of D4R units. Although CySH crystals typically contain significant amounts of crystal water, many of these water molecules can be removed (dehydrated) without structural collapse, allowing the synthesis of D4R-polysiloxane copolymers with regular structure in the silicone bridges linking the D4R units. This polymerization environment also limits the occurrence of unwanted side reactions.

In one approach, PSS-2 is synthesized by reacting tetrabutylammonium cyclosilicate hydrate (TBA-CySH) crystals, with idealized formula $[N(C_4H_9)_4]H_7[Si_8O_{20}]\cdot(5.33\ H_2O)$, with dimethyldichlorosilane vapor. In this case, the 3D structure of FIG. 2A is templated in the starting material, as TBA-CySH crystals are a hydrogen-bonded network of D4R units with geometric arrangement like that in the desired final product. During synthesis from TBA-CySH, the small cavities ('a' in FIG. 2A) typically contain a protonated water cluster while the large cavities ('b' in FIG. 2A) include six TBA cations, one in each window of its boundaries. The positive charges of these organic cations and the protonated water cluster compensate the negative charge of the silanolate groups on the D4R units. Upon reaction with dimethyldichlorosilane vapor and subsequent treatment with water vapor, the hydrogen bonds of the starting TBA-CySH crystals are replaced by dimeric dimethylsiloxane covalent linkers. The procedure is completed by vacuum evacuation of unreacted dimethyldichlorosilane and subsequent treatment with water vapor to complete cross-linking reactions, thus removing all chlorine atoms from the structure. Finally, a white product is recovered. The PSS-2 is calcined at 300° C. to remove TBA and triethylamine from its pores. Higher temperatures are avoided, however, to preserve the dimethylsiloxane groups, as the methyl groups of the siloxane bridges are thought to be lost at temperatures in the range of 550° C.

When fabricating a porous matrix from D4R units, tests have indicated that the crystal morphology depends on crystallization time. TBA-CySH crystals recovered after ten days are relatively shapeless, whereas crystals grown for more than twenty-one days exhibit distinct crystal faceting. However, regardless of crystal morphology, the materials exhibited identical microscopic and nanoporous structure. Furthermore, the chemical composition of the TBA-CySH crystals corresponded to $[N(C_4H_9)_4]_{1.2}[N(C_2H_5)_3]_{0.24}[Si_8O_{20}H_8]\cdot(5.6\text{-}6.6)[H_2O]$, which is close to the idealized composition of $[N(C_3H_9)_4]H_7[Si_8O_{20}]\cdot5.33H_2O$ obtained in absence of triethylamine. This close approximation of ideal stoichiometry is also an indication of a material with the desired regular structure shown in FIG. 2A.

The noted synthetic procedures are an example route to a robust, porous and interconnected material with internal recesses at the nanoscale of interest in the present invention to facilitate hyperpolarization transfer from source to target species. The nanoscale recesses may be loaded and unloaded with these species, and optional solvent or carrier fluid, according to schemes in FIG. 1. The procedures above yield PSS-2 with nanoscale pores (FIGS. 2A, C and D) at diameters of about 1-2 nm when n=2 in the dimethylsiloxane-based linkers (FIG. 2B, left). Another valuable feature of PSS-2 for the present invention is that its porosity can be tuned by varying n. For example, each added Si—O—Si unit increases the length of a linker by about 0.3 nm. This may facilitate optimization of the material employed for aspects such as distribution of hyperpolarized source and target species to nanopores within the material, for their admission and removal from the pores at convenient operating conditions (for example, of pressure and temperature), and for the physical conditions they experience while residing in the nanopores. For example, pore dimensions may be modified for more effective transfer of hyperpolarization from source to target species, and as needed, for relatively slow relaxation of the hyperpolarization both before and after the transfer.

Figure 4:
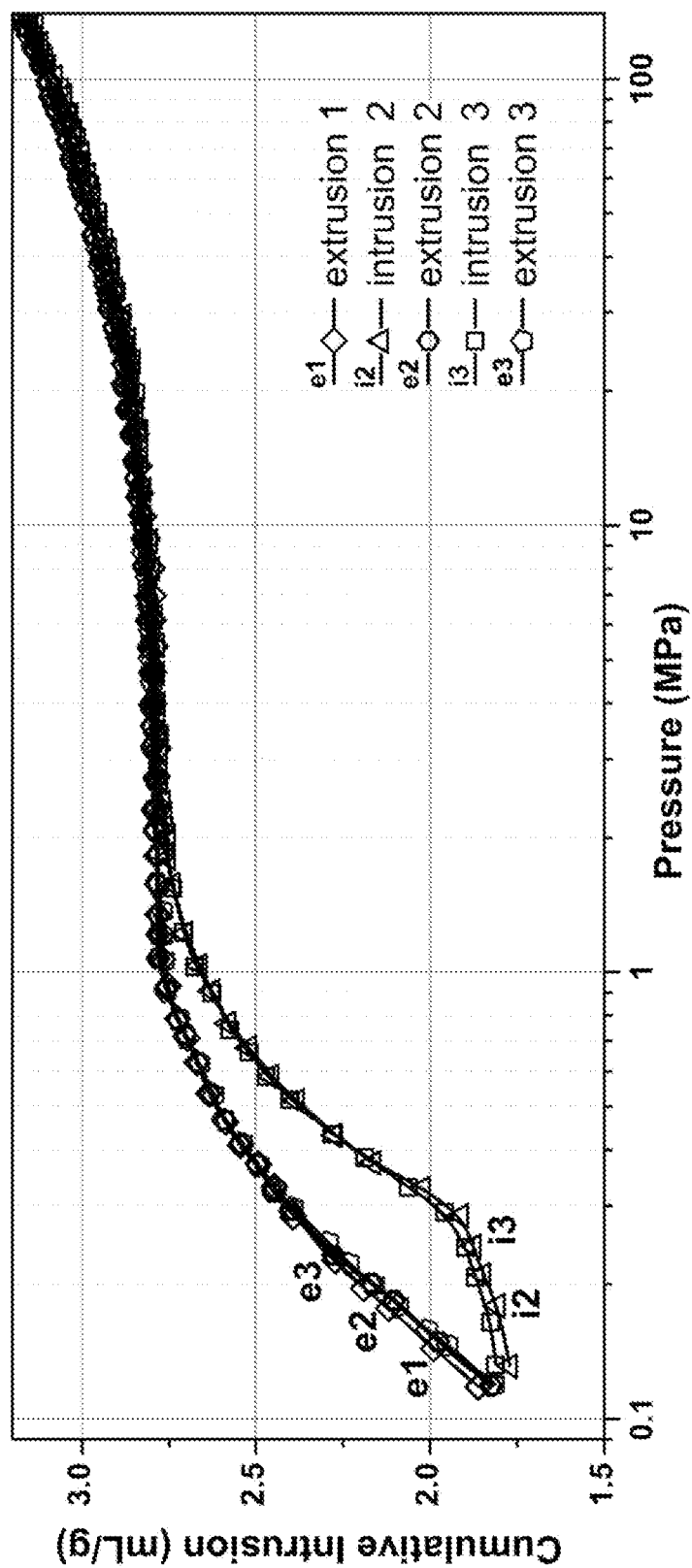
FIG. 4 is a plot showing pressure-driven loading (intrusion) and unloading (extrusion) of water into the nanoporous material, PSS-2. Data is shown for three successive intrusion-extrusion cycles, demonstrating reversible and reproducible loading and unloading using only a modest pressure cycle that results in a plateau of about 2.5 mL water loaded per gram PSS-2 over a pressure range of about 1.5 to 10 MPa (15-100 bar) above atmospheric. For purposes of the invention, such water handling may be used to deliver solvated hyperpolarized source and target species to and/or into nanoscale recesses of the material.

Results of experiments to demonstrate the suitability of PSS-2 for the present invention are detailed in FIGS. 4 and 5, which explore interactions of PSS-2 with aqueous solvent and parahydrogen, respectively. In each case, the PSS-2 sample used exhibited 89% connectivity between D4R units after the calcination step of its synthesis. Furthermore, $^{29}$Si NMR results indicated <2% free polydimethyl siloxane, <2% broken linkers and <1% collapsed D4R cubes. Additional details on both the synthesis and analysis of the material used in experiments of FIGS. 4 and 5 are as follows. TBA-CySH crystals were synthesized out of an aqueous solution of tetrabutylammonium hydroxide, tetraethylorthosilicate and triethylamine. Upon reaction with dimethyldichlorosilane these crystals were transformed into PSS-2. Thermogravimetrical analysis of the PSS-2 showed that calcining the material at 300° C. effectively removed all organics while leaving the dimethylsiloxane groups unaltered. $N_2$-physisorption and X-ray diffraction showed the PSS-2 to be a dense, amorphous material. The porosity and surface area of PSS-2 may be determined using $N_2$ physisorption with, respectively, the well-known t-plot method [as described in *Langmuir*, Vol. 30, No. 44, pp. 13266-74 (2014)] and BET (Brunauer-Emmett-Teller) analysis [as described in *Pure and Applied Chemistry*, Vol. 66, No. 8, pp. 1739-58 (1994)]. In the $N_2$ physisorption conditions, PSS-2 appears to be a dense material with a specific surface area of 5 m²/g, which is ascribed to external surface of the particles.

According to $^1$H decoupled single pulse magic angle spinning (MAS) NMR, the D4R units in this PSS-2 preparation were interlinked by short dimethylsiloxane chains. The $D^2/Q^4$ ratio was understood to be due to a roughly equal amount of siloxane chain bridges of two and three dimethylsiloxane groups. In an attempt to synthesize materials consisting of D4R units homogeneously linked by two dimethylsiloxane groups, the ratio of dimethyldichlorosilane to TBA-CySH parent material was reduced in the synthesis. The different materials were characterized using $^{29}$Si MAS NMR techniques providing evidence that they were partially transformed to PSS-2 wherein D4R units are always connected by a similar combination of short siloxane chain bridges. It was found that materials that underwent intermediate transformation to PSS-2 after a calcination step were the most porous. $^1$H decoupled $^{29}$Si single pulse MAS-NMR provided evidence that PSS-2-occluded TBA-CySH material mostly collapsed during the calcination step leaving behind voids in the PSS-2 material. One such an intermediately transformed PSS-2 material was synthesized, calcined and used in the high-pressure intrusion-extrusion experiments (FIG. 4) and in the p-H$_2$ stability tests (FIG. 5) described below.

The water intrusion-extrusion experiments demonstrate that, using moderate pressure cycles between about 0 and 3 bar, liquid water can be repeatedly loaded (intruded) and unloaded (extruded) from PSS-2. Such a process may be used to deliver solvated hyperpolarized source and target species to and/or into nanoscale recesses of the material. FIG. 4 provides data from three successive intrusion-extrusion cycles of water with PSS-2. This shows reproducible cycles with a plateau of about 2.5 mL water loaded per gram PSS-2 occurring over a range of about 1.5-10 MPa (15-100 bar). The critical pressure range, that is, where the rate of change is steepest, occurs over about 0.3-0.4 MPa (3-4 bar). Similar results were obtained with 20 M aqueous LiCl solution, where the plateau occurred over about 20-80 bar. Although, in comparison with pure water, approximately 10% lower total intrusion volume was achieved with this LiCl solution. Nonetheless, the similar performance of PSS-2 for loading of either pure water or a nearly saturated aqueous ionic solution demonstrates a very broad range of fluids compatible with pressure-driven intrusion-extrusion cycles for this material. That is of value for the invention, where it may be desirable to load and unload arbitrary fluid components into the nanoporous material. In that way, conditions experienced and provided by the components themselves may be tailored for positive impact on hyperpolarization transfer from source to a target species, and not limited by receptivity of the material to these species or a particular solution type containing them.

It is also noteworthy that the intrusion-extrusion data presented on water in FIG. 4 and also performed on LiCl solution was collected following an initial set showing a substantial compression of the powder on first intrusion event, a result ascribed to the collapse of part of the macroporosity. For the subsequent intrusion-extrusion cycles (FIG. 4), the material remained stable showing perfectly superimposable intrusion and extrusion curves. This reproducibility demonstrates that the material was able to withstand pressures of up to 200 MPa. Meanwhile, the critical pressures for intrusion-extrusion of both water and the LiCl solution in remaining (non-collapsed) macropores (D>50 nm) and mesopores (D=2-50 nm) are relatively low and readily achieved (intrusion pressure of up to 5 MPa and an extrusion pressure of 0.3 MPa). The material was able to take up a substantial amount of liquid in these pores (1 cm³/g for water and from 1.1-1.2 cm³/g for LiCl solution). Note that this use of 'mesopore' follows the classical definition introduced earlier and thus corresponds to the nanoporous regime of interest for this invention. The range of pore sizes filled over a given pressure regime was determined by the method of mercury porosimetry [as described in *Pure and Applied Chemistry*, Vol. 84, No. 1, pp. 107-136, 2012.] Moving to still higher pressures, from 5 to 200 MPa, the micropores (D<2 nm) of the material were filled with 0.5 cm³/g for water and 0.4 cm³/g for LiCl solution, respectively.

Additional key demonstrations of the value of PSS-2 to the present invention are given in FIG. 5, which explores the lifetime of p-H$_2$ during exposure to PSS-2. This is essential in order to demonstrate that the material itself does not quench the spin order of p-H$_2$. That is, after intrusion of p-H$_2$ to a material of use in this invention, the subsequently removed (extruded) hydrogen molecules consist of substantially the same enriched fraction of p-H$_2$ as was input to the material. This makes the material particularly effective as a container for this hyperpolarized gas in that the material itself does not rapidly destroy (quench) its hyperpolarized nature, leaving it available instead for transfer to a desired target.

Figure 5A:
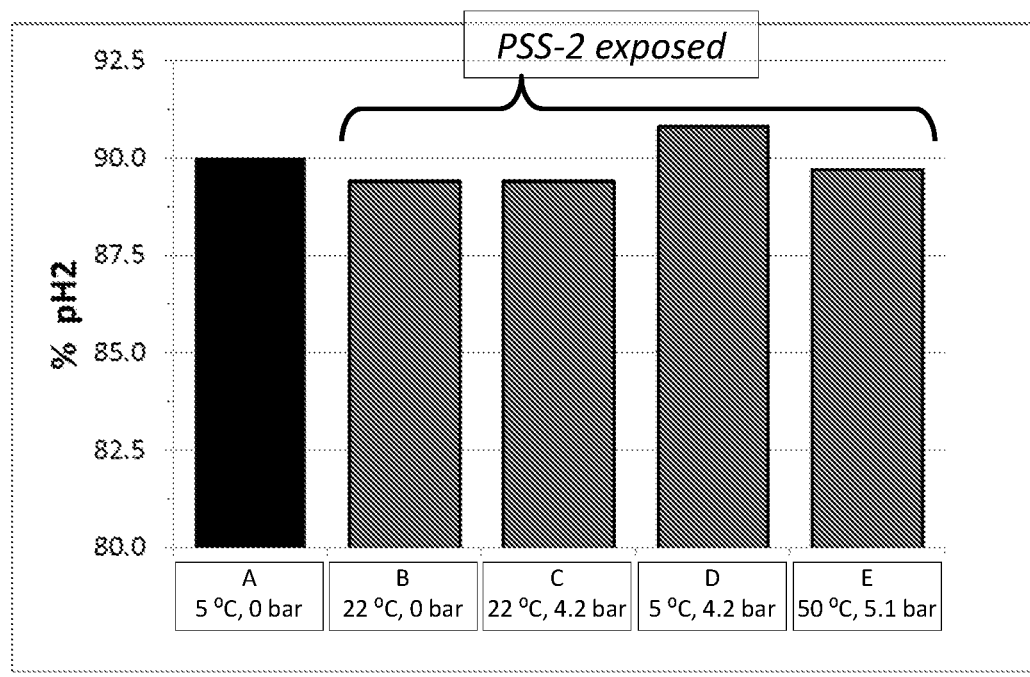
FIG. 5A is a bar graph showing the percentage of para-hydrogen (p-$H_2$) remaining after continuous flow through a chamber containing PSS-2 at various pairings of temperature (5 to 50° C.) and pressure (0 to 5.1 bar above atmospheric). A reference case is included in which PSS-2 was not present in the chamber and where conditions were at 5° C. and 0 bar (atmospheric pressure).
Figure 5B:
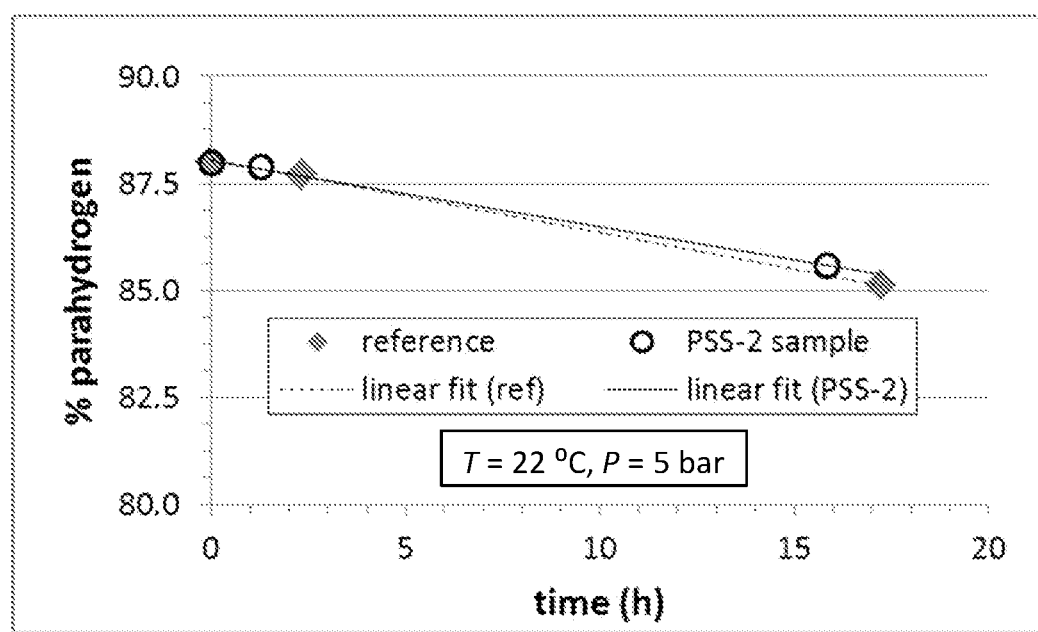
FIG. 5B is a plot showing the percentage of p-$H_2$ remaining after prolonged confinement in the chamber with PSS-2 or without it (labeled as "reference"). In repeated experiments, the confinement time was varied between 0 and 17 hours, all at 22° C. and a pressure of 5 bar.

Two experiment types are presented in FIGS. 5A and 5B. FIG. 5A explores the role of temperature and pressure on the relaxation of p-H$_2$ (towards its 25% equilibrium population) after flow-through exposure to PSS-2. FIG. 5B explores p-H$_2$ relaxation when confined in a chamber with PSS-2 for variable exposure time (up to 17 hours) in the particular case of 22° C. and 5 bar above atmospheric pressure. For both experiment types, hydrogen gas enriched to an initial p-H$_2$ level near 90% (and, thus, near 10% o-H$_2$) was obtained from a Bruker parahydrogen generator (BPHG) (manufactured by Bruker BioSpin Corp., Billerica, Mass.), and introduced to a valved chamber composed of black Delrin (polyoxymethylene) and of 0.4 cm³ volume. The chamber either contained 0.32 cm³ of PSS-2 or was left empty as a reference case. Standard analysis of the intensity of Raman rotational spectral features from p-H$_2$ and o-H$_2$ in the extruded gas was used to determine the percent p-H$_2$ present. Confinement durations far exceeded the typical time (second to tens-of-seconds) required for interaction and transfer of hyperpolarization from p-H$_2$ to target molecules using PHIP or NH-PHIP methods.

FIG. 5A is a bar graph showing the percentage of p-H$_2$ remaining after flowing p-H$_2$-enriched gas, at various pairings of temperature and pressure (5 to 50° C. and 0 to 8.9 bar above atmospheric), through a sealed chamber containing a 0.32 cm³ sample of PSS-2. Flow rates were similar in all cases (100-200 cc/min), with some variation according to the conditions of pressure and temperature. It should be noted, that unlike the case of water, H$_2$ (and p-H$_2$) gas permeates the PSS-2 material even at 0 bar, that is, at atmospheric pressure, and at all higher pressures represented in FIG. 5. The reference case (without PSS-2) included in FIG. 5A was run at 5° C. and 0 bar and showed no detectable change in p-H$_2$ level (90.0%) compared to that initially introduced. The same is true for PSS-2 exposure at 22° C. and either 0 or 4.2 bar, both yielding apparently insignificant changes of −0.06% in the p-H$_2$ level, which is near experimental uncertainty. Meanwhile, using similarly elevated pressure (4.2-5.1 bar) at either cooler (5° C.) or warmer (50° C.) temperature also yielded no significant change, +0.8 and −0.3%, respectively, versus the reference.

FIG. 5B explores the impact of PSS-2 on p-$H_2$ lifetime in greater detail for the case of confined exposure of 88% p-$H_2$ under conditions of 5 bar and 22° C. in the 0.4 $cm^3$ chamber. After 15 hours continuous PSS-2 exposure, only slight reduction (−2.4%) to approximately 85.6% p-$H_2$ was apparent. Similarly, 17 hours confinement to the chamber under the same conditions, but without PSS-2, yielded only −2.9% change to 85.1% p-$H_2$. FIG. 5B also shows linear fits for basic evaluation of the time series from both exposed and reference data sets. The slopes do not significantly differ, and thus the rates of ortho/para conversion are indistinguishable. These results reflect the well-known long lifetime for interconversion of ortho- and parahydrogen. More importantly, they highlight that PSS-2 has insignificant impact on the lifetime of p-$H_2$ under these conditions.

Figure 6A:
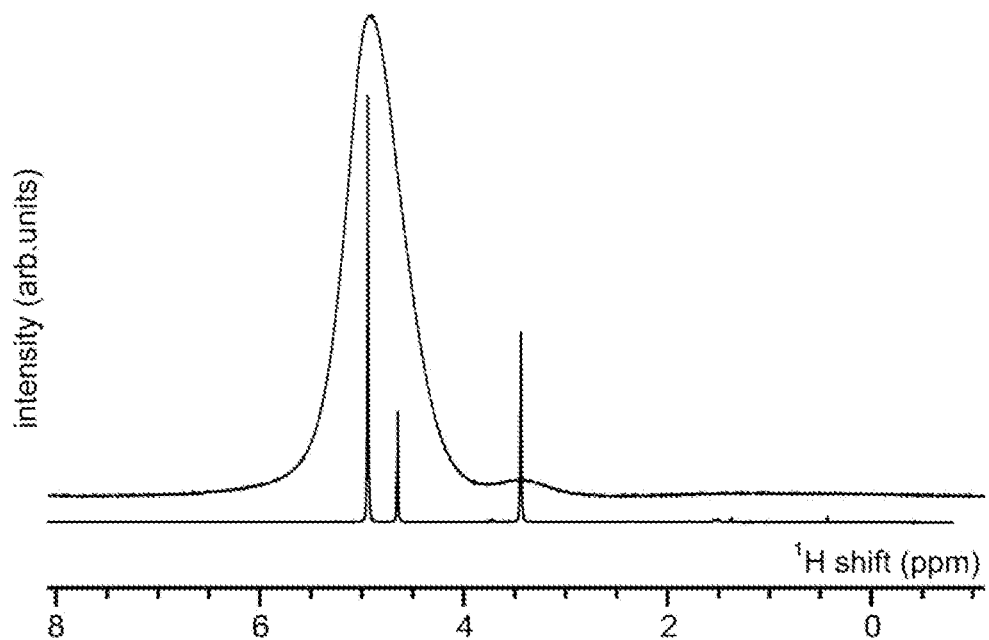
FIG. 6A is a plot with two solution-state $^1H$ NMR spectra of methanol-$d_4$ (99% deuteration level) saturated with $H_2$ (thermal 25:75 para:ortho ratio) at a pressure near 4 bar. The lower trace (sharp peaks) is the spectrum collected with this solution in an otherwise empty, standard NMR sample tube, whereas the upper trace (broad peaks) was collected in a sample tube that additionally contained a hydrophobic silica powder, specifically octadecyl carbon chain (C18)—functionalized silica. The silica material filled the NMR tube up to the full region of NMR detection, such that only the portion of the sample in intimate interaction with the material was characterized. In both spectra, $^1H$ NMR peaks correspond to o-$H_2$ at 4.55 ppm and the residual protons in methanol-$d_4$, which give a single peak at 4.8 ppm for the hydroxyl (—OH) proton and a tight quintet grouping at 3.3 ppm for the —$CD_2H$ proton. The dramatic differences in linewidth between upper and lower spectra can be explained by material-induced spatial order among methanol and $H_2$ molecules, leading to non-vanishing dipolar couplings in both the solvent and solvated gas.
Figure 6B:
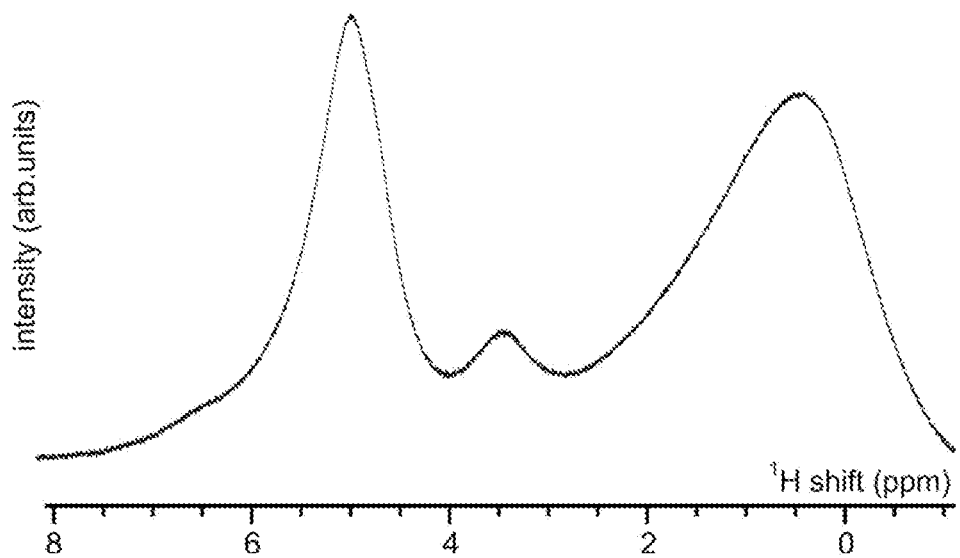
FIG. 6B is a plot with a solution-state $^1H$ NMR spectra of deuterated methanol (methanol-$d_4$) saturated with p-$H_2$ (enriched to near 90:10 para:ortho ratio) at a pressure of 4 bar in a sample tube that additionally contained PSS-2, filled in the NMR sample tube to the same degree as the silica in FIG. 6A. As in FIG. 6A, 4.8 and 3.3 ppm peak positions are apparent for hydroxyl and —$CD_2H$ in methanol. The PSS-2 introduces similar broadening as described with FIG. 6A from the C18-silica material. Unlike FIG. 6A, the o-$H_2$ peak is obscured here due to both its lower concentration and the broadening, while FIG. 6B also shows a unique peak near 1 ppm due to protons in the PSS-2 material. Also note that p-$H_2$ is NMR silent, thus does not provide a peak in the spectrum.

FIGS. 6A and 6B demonstrate a distinct and positive impact of the confinement of hydrogen, solvents and other small molecules within porous recesses of a material. FIG. 6A provides two solution-state $^1$H NMR spectra. Both are of methanol-$d_4$ (99% deuteration level) saturated with $H_2$ (thermal 25:75 para:ortho ratio) at a pressure of about 4 bar. The lower trace (sharp peaks) is the spectrum collected with this solution in an otherwise empty, standard NMR sample tube, whereas the upper trace (broad peaks) was collected in a sample tube additionally filled with a hydrophobic silica powder, specifically octadecyl carbon chain (C18)—functionalized silica. In both spectra, $^1$H NMR peaks correspond to o-$H_2$ at 4.55 ppm and the residual protons in methanol-$d_4$, which give a single peak at 4.8 ppm for the hydroxyl (—OH) proton and a tight quintet grouping at 3.3 ppm for the —$CD_2$H proton. FIG. 6B shows similar spectral broadening for the same type of sample, but with methanol and p-$H_2$ (enriched to near 90:10 para:ortho ratio) at a pressure of 4 bar, and filled with PSS-2 in the sample tube in place of the silica material.

The much broader lineshapes observed in the presence of the silica material can be explained by spatial ordering of the methanol and $H_2$ due to their pressure-induced confinement to recesses in the material. Such ordering introduces non-vanishing (residual) dipolar couplings, which spread the distribution of NMR frequencies that are exhibited by the small molecules. The ordering and consequent RDCs result from inhibited molecular motion, whereas free motion in isotropic solution-state conditions would average dipolar couplings to zero.

The broadening demonstrates that RDCs or other spin interactions may be introduced by porous materials such as PSS-2 and silica. Newly apparent couplings may be manipulated to effect transfers of spin polarization among nuclei by methods such as CP or TEDOR (Transferred Echo DOuble Resonance). This includes transfers between nuclei in different molecules, such as p-$H_2$ (hyperpolarization source) and accompanying molecular species targeted for hyperpolarization.

Altogether, the results of FIGS. 4, 5 and 6A-6B demonstrate the suitability of PSS-2 for the present invention. The material is shown to demonstrate behavior such as intrusion and extrusion over convenient, readily accessible pressure ranges, that can facilitate hyperpolarization protocols like those embodied in FIG. 1. Furthermore, PSS-2 even survives high pressures up to 200 MPa (20 bar), retaining the capability for reproducible intrusion-extrusion cycles over the more-modest range 1-10 bar. This property is rarely seen upon intrusion of liquids in porous materials such as zeolites, silica gels or metal-organic frameworks (MOFs). The ability of PSS-2 to take up water with dissolved reagents and catalysts allows for confinement of the reagents, introducing diffusion limitations during their physical and/or chemical interaction and subsequently releasing the physically or chemically altered products via a pressure swing cycle (i.e., dropping to a relatively low pressure).

In addition, the low-to-negligible impacts on p-$H_2$ lifetimes are also an essential feature. While many materials allow p-$H_2$ to transform to o-$H_2$, the retention of p-$H_2$ spin order at convenient operation temperatures is extremely difficult. For example, adsorption to high-surface area materials can allow rapid conversion of p-$H_2$ to o-$H_2$ and even storage of p-$H_2$ in macroscopic bottles requires careful selection of the material and/or internal coating of the storage vessel to avoid conversion. Here, p-$H_2$ stability tests have shown that the p-$H_2$ concentration was not affected after contact with PSS-2 in the temperature range of 5-50° C. and in the pressure range of about 0-5 bar. At room temperature and at a pressure of 4-4.5 bar, PSS-2 did not affect the p-$H_2$ concentration for even up to fifteen hours of contact.

Also important is that FIG. 6B demonstrates couplings that can enable polarization transfers from a hyperpolarized source to an accompanying target molecule. This was observed using PSS-2 under similar conditions of pressure, temperature and solvent as explored in FIGS. 4 and 5. That indicates a system and conditions that are simultaneously favorable for intrusion/extrusion, the avoidance of unproductive loss (relaxation of hyperpolarization), and the opportunity for productive transfer of hyperpolarization. Altogether, these results make a material like PSS-2 ideal for performing NMR or MRI sensitivity enhancement using transient, intimate interaction between parahydrogen and target species that are intended for later NMR or MRI analysis.

Depending on solvent and solute properties (such as polarity, sorption behavior) and on the chosen mode of operation (flow through vs. pressure swing), the properties of the nanoporous host material may be adapted to optimize the performance. For example, in a pressure-swing process using water as the solvent, preferentially the host material would generally present nonpolar interior surfaces. This avoids excessive attraction between the solution and the interior surfaces of the host, such that the minimum pressure segment of the swing cycle tends to result in expulsion of the previously intruded polar solution. The experiments described with FIG. 4 are representative of this case, corresponding to polar aqueous solution and nonpolar PSS-2 material. When instead operating a pressure-swing cycle with a nonpolar solvent, one would correspondingly utilize a nanoporous host with more polar interior surfaces. Independent of the mode of operation (that is, for either flow-through or pressure-swing-cycle modes), one may similarly benefit by utilizing a nanoporous host whose interior-surface polarity is tailored to a specific application. In this way, one may tune the residence time of the various species (solvent, source and target) within the nanoporous chambers, and vary the degree and nature of their interactions with the pore walls and each other, all to the effects of improved source-to-target hyperpolarization transfer and minimized or limited spin relaxation.

Additional Experimental Details on Synthesis and Characterization

Synthesis of TBA-CySH

In an example of synthesis of TBA-CySH, as used for PSS-2 synthesis, 54.8 g of Tetraethylorthosilicate (TEOS) (Acros 98%) was slowly added to a stirred aqueous solution of triethylamine (42.2 g) and Tetrabutylammonium Hydroxide (58.5 g, 40 wt % in water). After allowing the mixture to stir for ten days, the formed crystals were recovered by centrifugation for 2 hours at 12,000 rpm. Similar procedures with approximately four times scale-up and about double duration of the stirring period were also demonstrated to yield TBA-CySH crystals suitable for subsequent production of PSS-2.

Synthesis of PSS-2

In an example of the synthesis of PSS-2, approximately 180 milligrams of TBA-CySH crystals (recovered after ten days) were dried under vacuum (1 mbar) in a closed 1 L glass flask. After 72 hours of drying, variable amounts of dimethyldichlorosilane were added, namely, 90 µL, 178 µL, 185 µL, 236 µL and 388 µL, respectively. The silane was added into a recipient inside the flask so that direct contact with the crystals was prevented. After reacting for six days the excess silane was removed under vacuum during 24 hours. Finally, the synthesis was terminated by the addition of 6 ml of water, for the case where 388 µL of dimethyldichlorosilane was also added, or 6 ml of an aqueous ammonia solution (25 wt %) for all other samples. Twenty-four hours later the glass flask was opened and the white PSS-2 powder collected.

The PSS-2 sample that was used in the high-pressure intrusion-extrusion cycles of liquids and in the p-$H_2$ stability tests was synthesized as follows. 8.5 grams of TBA-CySH crystals (recovered after 21 days) were dried under vacuum (1 mbar) in a desiccator (13 L). After 72 hours of drying, 14 mL of dimethyldichlorosilane was added. The silane was added into a recipient inside the desiccator so that direct contact with the crystals was prevented. After reacting for two weeks, the excess silane was removed under vacuum during twenty-four hours, and the reaction was stopped by adding 10 mL of an aqueous ammonia solution (25 wt %). Twenty-four hours later the desiccator was opened and a white powder was collected. In each case, calcined PSS-2 powders were heated to 300° C. under nitrogen flow for 3 hours and then kept at 100° C. overnight.

Characterization of PSS-2 Material

Solid state nuclear magnetic resonance spectra of TBA-CySH and PSS-2 particles (before and after water-sorption experiments) were recorded on a 300 MHz Bruker Avance III spectrometer (manufactured by Bruker BioSpin Corp., Billerica, Mass.) at a resonance frequency of 59.6 MHz for $^{29}$Si. The samples were spun at 10 kHz in a 4 mm zirconia rotor aligned to the magic angle (54.74°) with respect to the applied magnetic field. For the $^1$H-decoupled $^{29}$Si single pulse magic-angle spinning (MAS) NMR spectra, 448 scans were recorded with a recycle delay of 513.6 s and a 90° pulse of 3.75 µs. Decoupling was performed by using a Spinal-64 sequence for the $^1$H→$^{29}$Si cross polarization (CP) in CP-MAS-NMR spectra recorded in 448 scans with a recycle delay of 6 s, a 90° pulse on $^1$H of 3 µs and a CP contact time of 3.5 ms. Nitrogen adsorption/desorption isotherms of the calcined materials were recorded at −196° C. using a Micromeritics Tristar apparatus. The specific surface area (BET) and microporous volume (ρV) were calculated using the BET and t-plot methods, respectively.

The water intrusion-extrusion experiments on PSS-2 were performed at room temperature over three cycles using a modified mercury porosimeter (Micromeritics Model Autopore IV). The cell containing the water/PSS-2 system consists of a polypropylene cylinder of 2 cm$^3$ sealed by a mobile piston. This cell is introduced in the 15 cm$^3$ glass cell of the porosimeter which is filled with mercury. The volume variation is determined through a capacity measurement which depends on the mercury height in the capillary tube of the glass cell. The experimental intrusion-extrusion curve is obtained after subtraction of the curve corresponding to the compressibility of pure water. The pressure is expressed in megapascal (1 MPa=10 bar) and the volume variation in milliliter per gram of sample (mL g$^{-1}$). The p-$H_2$ was generated by a Bruker ParaHydrogen Generator (BPHG), which converts the 25/75 room-temperature mix of p-$H_2$ and o-$H_2$ from in hydrogen gas into approximately 90/10 p-$H_2$/o-$H_2$. The starting gas was 99.999% $H_2$ from either a high-purity cylinder or an electrolytic source accompanying the BPHG. A volume of 0.32 cm$^3$ PSS-2 (55% linked pre-calcination, and 89% after calcination and as used in p-$H_2$ experiments) was put in a Black Delrin container with a total volume of 0.4 cm$^3$. The temperature of the container was maintained at set points between 5 and 50° C. and the internal p-$H_2$ pressure was set to a value between 0 (atmospheric) and 8.9 bar above atmospheric pressure. The concentration of remaining p-$H_2$ was determined by standard methods using Raman spectroscopy to determine the ratio of o-$H_2$ to p-$H_2$.

The invention claimed is:

1. A method of enhancing the nuclear spin polarization of target molecules, the method comprising:
providing a hyperpolarized source material;
transferring the source material and the target molecules into a porous matrix with recesses of distinctly different sizes, a first group of recesses functioning as storage for the source material and having an average diameter in any direction of 2-5 nm, and a second group of recesses, larger than those of the first group, that function as chambers for accommodating the source material and the target molecules together while hyperpolarization is transferred from the source material to the target molecules, the second group of recesses having an average diameter of less than 20 nm;
confining the source material and target molecules in recesses of the matrix under external pressure for a predetermined period of time; and
removing the target molecules from the porous matrix.

2. A method according to claim 1 wherein the source material comprises parahydrogen.

3. A method according to claim 1 wherein said external pressure is substantially constant during said predetermined period of time.

4. A method according to claim 1 wherein said external pressure is modulated between high and low values.

5. A method according to claim 4 wherein said external pressure varies in a cyclic manner.

6. A method according to claim 1 wherein the porous matrix comprises a D4R polysiloxane copolymer.

7. A method according to claim 6 wherein the porous matrix comprises polyoligosiloxysilicone number two (PSS-2).

8. A magnetic resonance enhancement system for enhancing the nuclear spin polarization of target molecules comprising:
a hyperpolarized source material;
a porous matrix into which the source material is transferred together with the target molecules, the porous matrix having recesses of distinctly different sizes, a first group of recesses functioning as storage for the source material and having an average diameter in any direction of 2-5 nm, and a second group of recesses, larger than those of the first group, which function as chambers for accommodating the source material and the target molecules together while hyperpolarization is transferred from the source material to the target molecules, the second group of recesses having an average diameter of less than 20 nm; and a pressure source that provides an external pressure that forces the source material and target molecules into co-confinement in recesses of the matrix for a predetermined period of time prior to removal of the target molecules from the porous matrix.

9. A system according to claim 8 wherein the source material comprises parahydrogen.

10. A system according to claim 8 wherein the pressure source applies a substantially constant pressure during said predetermined period of time.

11. A system according to claim 8 wherein the pressure source modulates said external pressure between high and low values.

12. A system according to claim 11 wherein the pressure source varies said external pressure in a cyclic manner.

13. A system according to claim 8 wherein the porous matrix comprises a D4R polysiloxane copolymer.

14. A system according to claim 13 wherein the porous matrix comprises polyoligosiloxysilicone number two (PSS-2).

* * * * *